(12) United States Patent
He

(10) Patent No.: US 7,077,946 B2
(45) Date of Patent: Jul. 18, 2006

(54) HIGH THROUGHPUT MULTI-CHANNEL ROTATING DISK OR RING-DISK ELECTRODE ASSEMBLY AND METHOD

(75) Inventor: Ting He, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 228 days.

(21) Appl. No.: 10/713,242

(22) Filed: Nov. 14, 2003

(65) Prior Publication Data

US 2005/0103645 A1    May 19, 2005

(51) Int. Cl.
*G01N 27/42* (2006.01)
(52) U.S. Cl. .................. 205/775; 204/409; 204/434; 204/435
(58) Field of Classification Search ............... 204/400, 204/409, 434, 435; 205/775
See application file for complete search history.

(56) References Cited

U.S. PATENT DOCUMENTS 4,911,794 A * 3/1990 Parce et al. ............... 205/778

6,827,839 B1 * 12/2004 Sonnenberg et al. ........ 205/775

FOREIGN PATENT DOCUMENTS

WO        WO 01/25774 A1 *    4/2001

* cited by examiner

*Primary Examiner*—Kaj K. Olsen
(74) *Attorney, Agent, or Firm*—Rankin, Hill, Porter & Clark LLP; Mark E. Duell

(57) ABSTRACT

An electrochemical cell assembly including a plurality of testing cells, a reference cell, and fluid connections between the testing cells and the reference cell. Each of the testing cells includes a working electrode, which is a rotating disk or ring-disk electrode, and a counter electrode. A chemical composition, whose intrinsic kinetic properties under defined mass-transfer are to be investigated, is deposited on the working electrode. The reference cell holds a reference electrode that serves as a common reference electrode for each of the testing cells. The assembly permits simultaneous testing of many chemical compositions under identical environment.

20 Claims, 4 Drawing Sheets

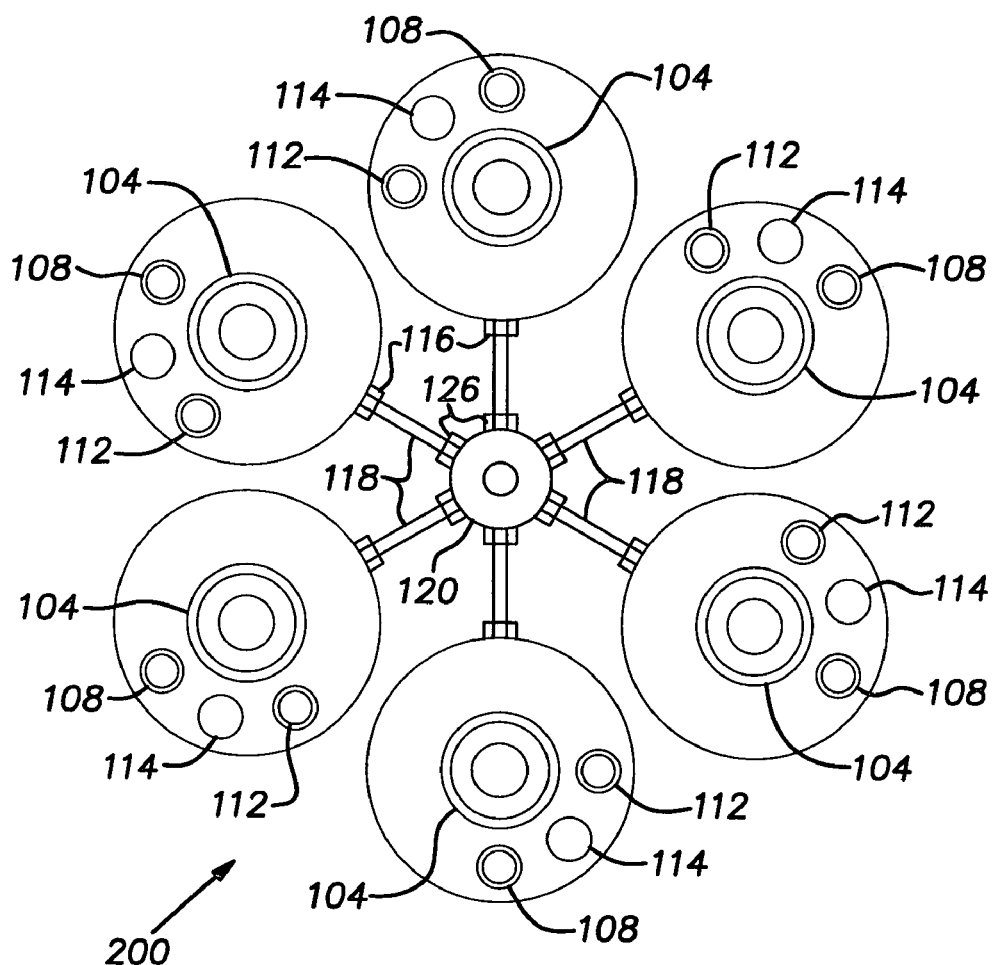
FIG. 5
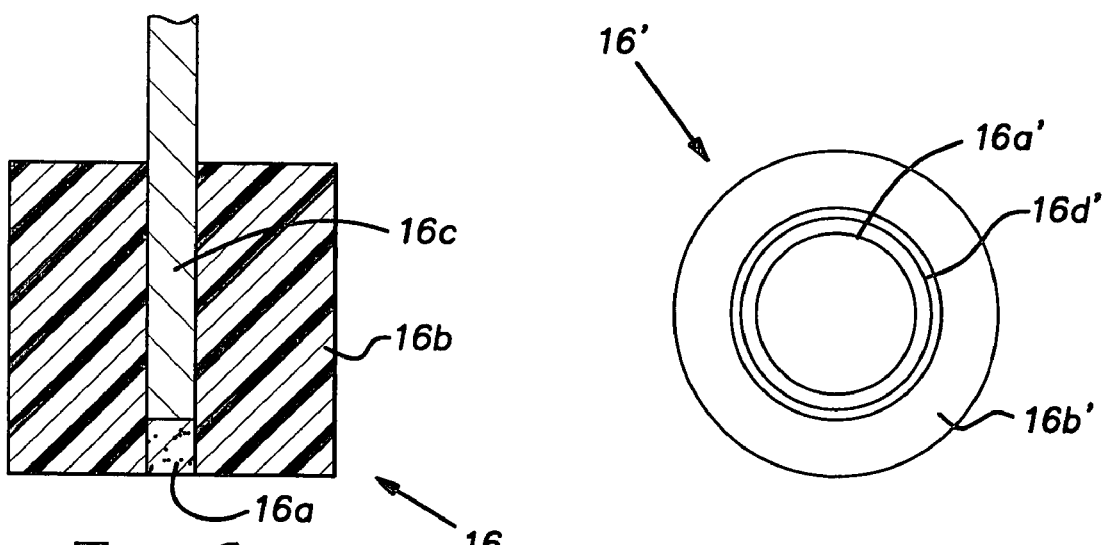
FIG. 6A
PRIOR ART
FIG. 6B
PRIOR ART

US 7,077,946 B2

HIGH THROUGHPUT MULTI-CHANNEL ROTATING DISK OR RING-DISK ELECTRODE ASSEMBLY AND METHOD

BACKGROUND OF THE INVENTION

1. Field of the Invention

The present invention pertains generally to electrochemical testing assemblies and, more particularly, toward multi-channel rotating disk or ring-disk electrode assemblies and associated testing procedures.

2. Description of Related Art

Generally, a three-electrode electrochemical cell includes a glass vessel holding a working electrode, with a counter electrode and a reference electrode in separate compartments. The electrodes are immersed in a testing solution, such as sulfuric acid, and a reference potential is applied between reference and working electrodes, whereas a current is established between the working and counter electrodes. This setup is used in basic research to investigate the kinetics and mechanisms of the electrode reaction occurring on the working electrode surface.

In some testing applications, a rotating disk electrode (RDE) or rotating ring-disk electrode (RRDE), which are hereinafter collectively referred to as the "RDE/RRDE", is used as the working electrode in the three-electrode cell. RDE/RRDE are well known in the art and are commercially available from several sources, such as Princeton Applied Research of Oak Ridge, Tenn.

The RDE/RRDE is a specialized hydrodynamic electrode used in the study of the kinetics and mechanisms of electrode reactions for ensuring a known and controllable mass-transfer to the electrode. The mass-transfer is achieved by using a flat disc electrode that is rotated in the testing solution, resulting in a defined hydrodynamic boundary layer. Typically, the RDE/RRDE is coated with a chemical composition whose kinetic parameters in an electrochemical reaction are to be determined. More specifically, thin films of chemical compositions are applied to the electrode surface of the RDE/RRDE, and the inherent electron-transfer characteristics of the chemical compositions are determined in the testing procedure. Conventionally, such tests are very time consuming due to the electrochemical cleaning and gas purging processes, but yield valuable information of the intrinsic electrochemical properties and kinetics so as to warrant further study.

A conventional three-electrode cell testing apparatus 10 is illustrated in FIGS. 1–2, and is shown to include a glass vessel 12 having a generally central port 14 that receives the working electrode 16, a first laterally disposed port 18 that receives a counter electrode 20, and a second laterally disposed port 22 that receives a reference electrode 24. The glass vessel 12 also typically includes a gas inlet port 26 for saturation of the testing solution 30 via a bubbling assembly 27 prior to a test procedure, as well as additional ports 28 for ventilation and gas flowing purposes. The glass vessel 12 holds the testing solution 30, such as sulfuric acid, in which the working electrode 16 is submersed and with which the counter and reference electrodes 18, 22 in separate compartments communicate.

With reference to FIGS. 6A–6B, the working electrode 16 is a RDE (FIG. 6A, 16) or a RRDE (FIG. 6B, 16'), which is conventionally formed as a disk 16a or ring-disk 16a', 16d of electrode material, such as gold, glassy carbon, or platinum, that is imbedded in a rod of insulating material 16b (16b'), such as polytetrafluoroethylene (PTFE) or low expansion oxides. For testing purposes, the electrode material 16a (16a') is coated (via a plasma deposition process, chemical vapor deposition process, powder ink or the like) with a chemical composition to be tested. The RDE/RRDE shaft 16c, which is electrically connected to the electrode material 16a (16a', 16d), extends from the insulating material 16b (16b') and is mechanically connected to a motor 32 that rotates the working electrode 16 (16') at a stable, high speed (i.e., 100–8000 rpm), which leads to a well-defined solution flow pattern of mass transfer. In this regard, it is noted that maintenance of the rotary speed is important as this speed is directly related to flow pattern and laminar flow layer parameters at the electrode surface, and thereby affects the electron-transfer properties under investigation. In any event, the RDE/RRDE, which are collectively referred to herein as the working electrode 16, is only used for a single testing procedure.

The reference electrode 24 has a well-known and stable equilibrium electrode potential, and provides a reference point against which the potential of the working electrode 16 is applied. Such reference electrodes are well known in the art and are readily commercially available from several sources, including Princeton Applied Research. Although the reference electrode 24 is received within the glass vessel 12, the reference electrode is typically, and more specifically, disposed within a double bridge tube assembly 25 that is illustrated in FIG. 7.

The double bridge tube assembly, which is hereafter referred to as the reference electrode assembly 25, includes the reference electrode 24 with the first bridge tube 24a and a second bridge tube 24b that protects the testing solution 30 from contamination by the reference electrode solution 30a. Each of the bridge tubes 24a, 24b holds a solution 30a, 30b, respectively, and includes a bridge, which are schematically illustrated and referred to as 24a', 24b', respectively. Normally the solution 30b in the second bridge tube 24b is the same as the testing solution 30. The bridges 24a', 24b' are typically made from VYCOR frit that prevents contamination of the testing solution 30, which could result from the leakage of the reference solution 30a. Accordingly, the reference solution 30a surrounding the reference electrode 24 is doubly isolated from the testing solution 30 via the bridges 24a', 24b'. Although the reference electrode 24 is reusable, and may be used for multiple testing procedures, it must be periodically tested to ensure that the electrode potential has not drifted over time.

Strictly speaking, there can be a small change in the potential of the reference electrode 24 depending on the electrolyte because of the presence of a liquid-junction potential. The liquid-junction potential is minimized by the use of high concentration solution, such as potassium chloride, as the solution 30a when the reference electrode 24 is a saturated calomel electrode.

The counter electrode 20 is used to make an electrical connection to the electrolyte or testing solution 30 (sulfuric acid) so that a current can be established between the working electrode 16 and the counter electrode 20. The counter electrode 20 is usually made of inert materials (noble metals or carbon/graphite) to avoid its dissolution. Typically, the counter electrode 20 has high surface area and is disposed within its own bridge tube or chamber 20a that includes a frit bridge 20b. The counter electrode bridge tube 20a is filled with a solution 30c, which is preferably identical to the testing solution 30 used in the vessel 12 and the testing solution 30b used in the second bridge tube 24b of the reference electrode assembly 25, while the solution 30a used in the first bridge tube 24a of the reference electrode assembly 25 may be different depending, in part, upon the particular reference electrode 24.

Before a testing procedure in which the kinetics and mechanisms of electrode reaction will be investigated, the deposited material on the surface of the working electrode 16 needs to be cleaned. Therefore, the working electrode 16, which is coated with a chemical composition whose properties are to be tested, is inserted into the testing solution 30 in the glass vessel 12, and the reference electrode assembly 25 and counter electrode assembly are inserted into the glass vessel 12. The testing solution 30 is saturated with a suitable gas, such as argon or nitrogen, via the bubbling assembly 27 to purge the testing solution 30. Thereafter, the chemical composition on the working electrode is cleaned by the cyclic voltammetry in a desired potential region repeatedly. Thereafter, the solution is saturated with a required gas, such as oxygen or hydrogen, depending on the properties to be measured, through bubbling. Then, the RDE/RRDE is rotated at a stable, high speed by the motor 32. By sweeping a potential between working electrode 16 and reference electrode 24, a current is established between the counter electrode 20 and the working electrode 16 in the solution and is recorded.

While the aforementioned well-known testing apparatus and associated testing method has proven to be satisfactory and reliable, it suffers from several significant disadvantages. First, the testing procedure is relatively long (1–2 hours) and requires significant set-up in order to reliably reproduce the testing environment, which is vital to having reliable, repeatable results. Second, only one working electrode-mounted chemical composition may be tested during any given testing procedure. Third, the reference electrode may need to be calibrated between successive tests to account for drift of the reference potential, as may occur over time.

While these disadvantages are relatively minor when testing a small number of chemical compositions, they prove to be major disadvantages when testing thousands of compositions and wherein some of the thousands of compositions may need to be tested multiple times. Therefore, there exists a need in the art for an apparatus and method that permits multiple chemical compositions to be tested simultaneously in a three-electrode electrochemical cell.

SUMMARY OF THE INVENTION

The present invention is directed toward a method and apparatus that permits simultaneous testing of plurality chemical compositions in a three-electrode electrochemical cell assembly that employs multiple rotating disk/rotating ring disk electrodes as the working electrodes.

In accordance with the present invention, an electrochemical cell assembly includes a plurality of testing cells, a reference cell, and fluid connections between each of the testing cells and the reference cell. Each of the testing cells includes a working electrode, which is a rotating disk or ring-disk electrode, and a counter electrode, whereas the reference cell includes a reference electrode assembly.

In further accordance with the present invention, each of the working electrodes is connected to a rotator so as to be rotatably driven by the motor. A controller is provided to control the speed of rotation of the working electrode. When individual motors are used to rotate each working electrode, the controller is adapted to control the motors such that the rotational speed of the working electrodes may be controlled to be identical to one another.

BRIEF DESCRIPTION OF THE DRAWINGS

These and further features of the invention will be apparent with reference to the following description and drawings, wherein:

FIG. 5 is a schematic plan view of the electrochemical cell assembly according to the present invention;

FIG. 6A is a schematic cross-sectional bottom view of a conventional rotating disk electrode;

FIG. 6B is a schematic bottom view of a conventional rotating ring disk electrode;

DETAILED DESCRIPTION OF THE PREFERRED EMBODIMENTS

Figure 1:
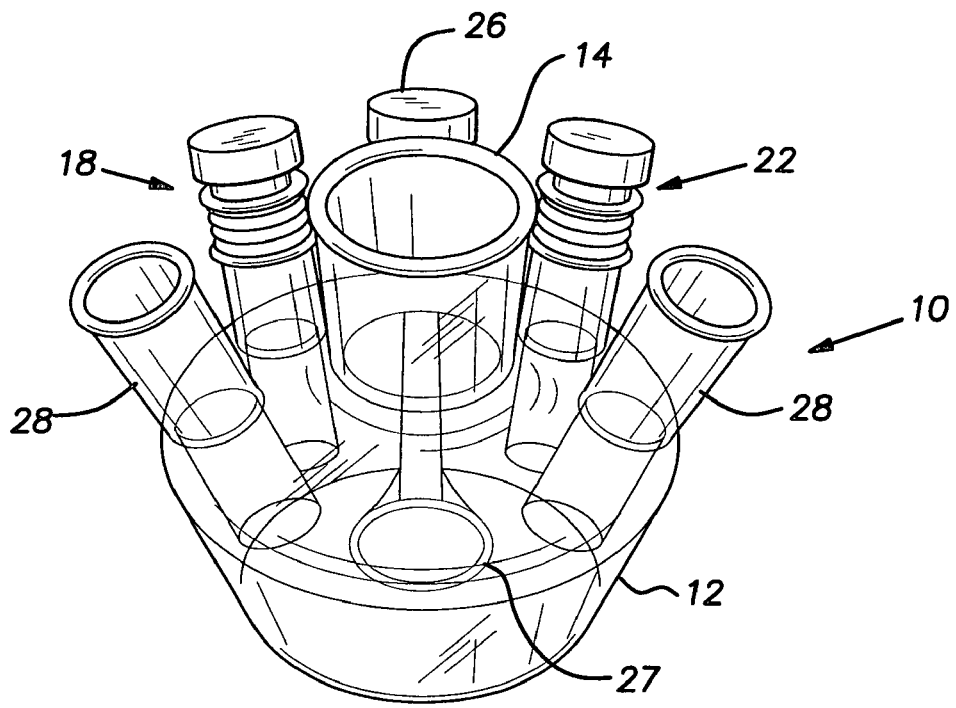
FIG. 1 is a perspective view of a conventional three electrode electrochemical cell.
Figure 2:
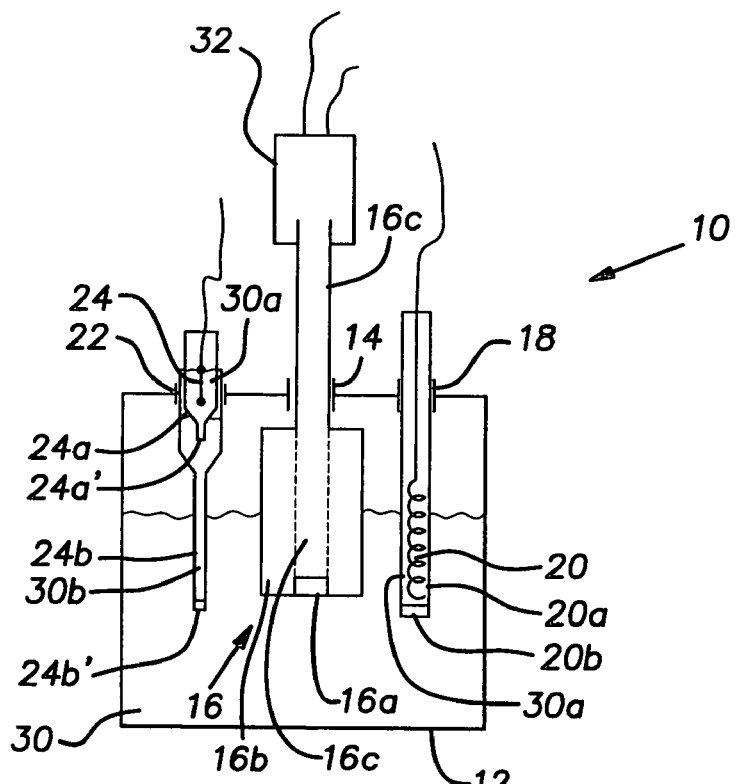
FIG. 2 is a schematic view of the conventional cell of FIG. 1.
Figure 3:
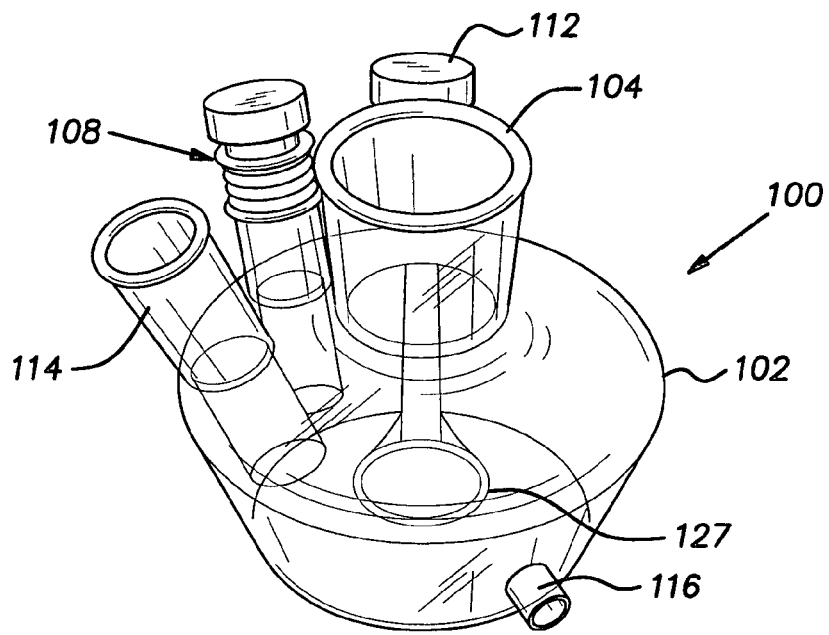
FIG. 3 is a perspective view of an electrochemical cell according to the present invention.

With reference to FIG. 3, an electrochemical cell 100 according to the present invention (referred to hereinafter as the "testing cell") is shown to include a glass vessel 102 having a generally central port 104 that receives a working electrode 106 and a laterally disposed port 108 that receives a counter electrode 110. The testing cell 100 also typically includes a gas inlet port 112 for bubbling/saturation of the testing solution prior to a test procedure, as well as additional ports 114 for ventilation and gas flowing purposes. The testing cell 100, as described to this point, is generally conventional.

The testing cell 100 also includes a port 116, which preferably is at a level close to, or slightly below, the level of the working electrode 106. The port 116 receives a pipe 118 that forms a passageway for communication with a reference cell 120, which holds a reference electrode 124. As will be apparent from the following discussion, the reference electrode 124 serves as a common reference electrode for a plurality of working electrodes 106 and, as such, is shared by a plurality of testing cells 100. Accordingly, an individual reference electrode for each testing cell 100 is not necessary with the present invention.

Figure 4:
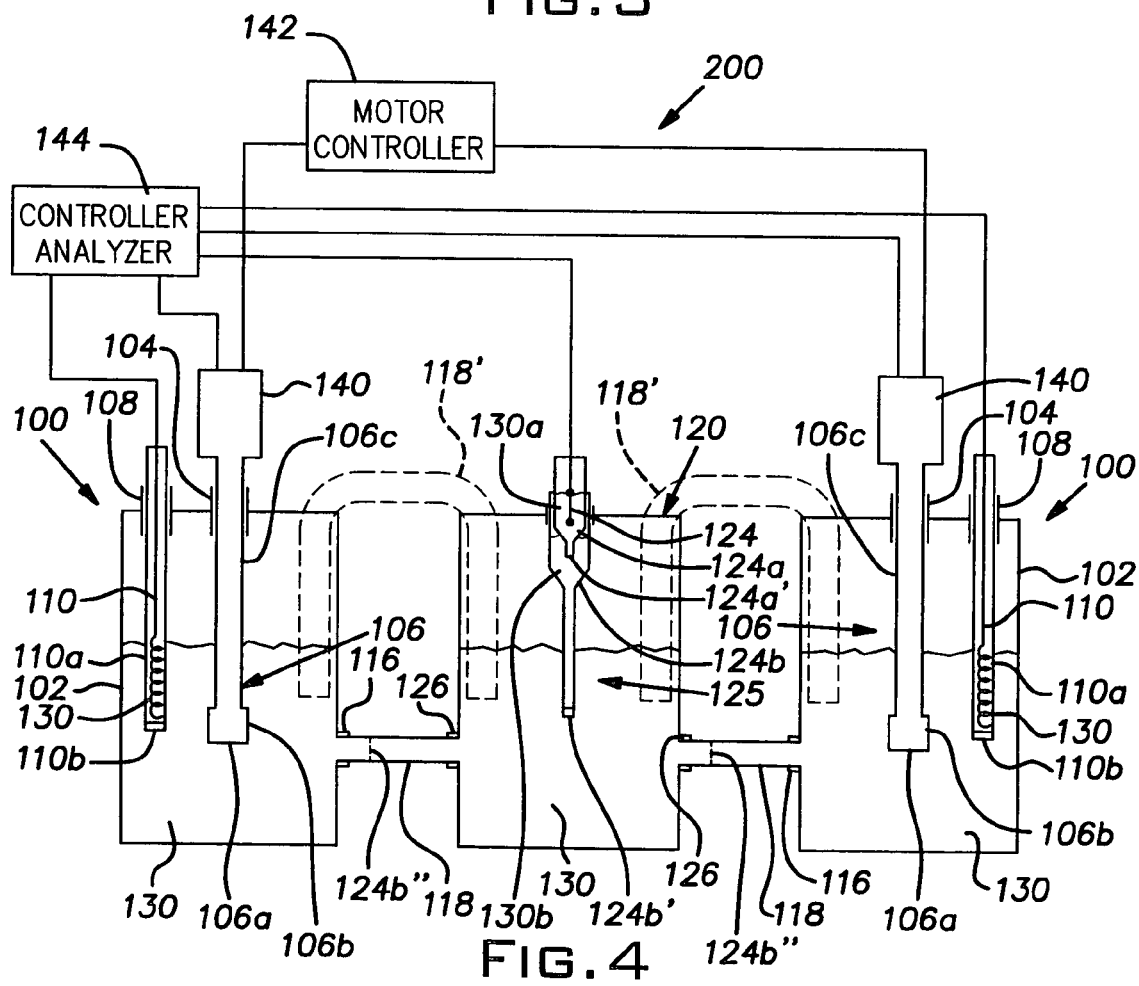
FIG. 4 is a schematic partial elevational view of an electrochemical cell assembly according to the present invention.
Figure 7:
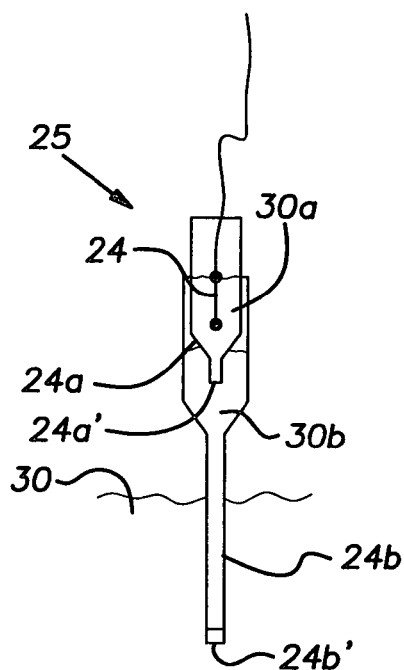
FIG. 7 is a schematic cross-sectional view of a conventional double bridge reference electrode assembly.

With reference to FIG. 4, the electrochemical cell assembly 200 according to the present invention is shown to include a plurality or array of electrochemical cells (testing cells 100, such as shown in FIG. 3) and a single or common reference cell 120. The reference cell 120 includes a double bridge assembly 125 that receives the reference electrode 124. The double bridge assembly 125 is generally conventional, and includes an inner bridge tube 124a and an outer bridge tube 124b. The inner bridge tube 124a is filled with a reference solution 130a. The outer bridge tube 124b is also filled with a testing solution 130b, which is identical to the testing solution 130 in the testing cell 100. Each of the inner and outer bridge tubes 124a, 124b include a bridge 124a', 124b' (preferably formed from VYCOR frit) to isolate the interior of the bridge tubes 124a, 124b so as to avoid contaminating the testing solution 130 of the testing cell 100.

Depending upon the type of reference electrode 124 used in the particular test, the reference solution 130a may be similar to the testing solution 130 (i.e., sulfuric acid) or may be different from the testing solution 130. For example, when a Mercury-Mercurous Sulfate (MMS) reference electrode is used, the reference solution 130a is sulfuric acid of higher concentration than that of the testing solution 130. On the other hand, when a Saturated Calomel (SCE) reference electrode is used, the reference solution 130a is potassium chloride, while the testing solution remains sulfuric acid, in which case the illustrated double bridge construction is necessary.

The reference cell 120 is in fluid communication with each of the testing cells 100 via the pipes 118. Preferably, the reference electrode 124 is disposed in the double bridge assembly 125, which is immersed in the testing solution 130 (sulfuric acid) contained within the testing cells 100, the pipes 118, and the remainder of the reference cell 120. As noted before, the double bridge assembly 125 includes a pair of bridges 124a', 124b' or filters that fluidly isolate the reference solution 130a from the testing solution 130, while permitting electrical connection or communication therebetween. It is assured that the distance between reference electrode 124 and each working electrode 106 is the same.

Although it is preferred to fluidly isolate the solution in reference electrode 124 in the double bridge assembly 125, and thereby provide redundant isolation from the testing solution 130 by means of the bridges 124a', 124b', it is considered apparent that the outer bridge tube 124b, and its associated bridge 124b', could be disposed of and that this isolation function performed by a bridge 124b" disposed within each of the pipes 118, or at one end of the pipes 118, as illustrated by dashed lines in FIG. 4. Further, while the pipes 118 are preferred, it is contemplated that these pipes could be replaced with siphon-type fluid connections 118', which are preferred by some researchers.

It is important to note that with a common reference electrode according to the present invention, an array of testing cells 100 can be employed. While the array depicted in FIG. 5 includes six testing cells, this is only for purposes of clarity and brevity. Rather, it is contemplated that the array may consist of 8, 16, 64, 96, 128 or any number of testing cells 100 that may be physically disposed around the reference cell 120. For example, the testing cells 100 may occupy several concentric rings or rows surrounding the reference cell 100. It is further noted that the testing cells 100 may be disposed vertically above and below the reference cell 120.

Each of the testing cells 100 has a working electrode 106 and a counter electrode 110. Preferably, the counter electrode 110 is disposed on the side of the working electrode 106 opposite to the connection of the pipe 118 with the testing cell 100, as illustrated in FIGS. 4–5.

The counter electrode 110 is conventional in design, and is disposed within a bridge tube or compartment 110a that includes a frit bridge 110b.

The working electrode 106 is a conventional RDE/RRDE having an electrode material 106a imbedded in an inert insulating body 106b. A metal shaft 106c extends from the body 106b and electrically connects the electrode material 106a to a controller/analyzer 144, discussed hereinafter. A chemical composition, whose electron transfer characteristics are to be examined, is coated, via known deposition techniques, on the outer surface of the electrode material 106a. The working electrode shaft 106c is secured to a rotator 140 that drives the working electrode 106 at a stable, verifiable rotational speed, such as between about 100–8000 rpm or more. The rotator 140 of the array of testing cells 100 may be a motor or may be a device that is magnetically or mechanically driven by a master motor, as described hereinafter.

In use, the reference electrode 124 is disposed within the reference cell 120, and the reference cell 120 is connected to each of the testing cells 100 via a pipe 118, as illustrated. A counter electrode 110 and working electrode 106 are inserted into each testing cell 100, and the working electrode 106 is rotatably secured to its associated rotator 140. In the embodiment illustrated in FIG. 4, the rotator 140 is a motor that is controlled by a motor controller 142. Preferably, a multi-channel potentiostat 144 (such as sold as a Potentiostat/Galvanostat by Princeton Applied Research and as a MultiStat by Solartron Analytical of Houston, Tex.) is used to apply the desired potential to the electrodes during the testing procedure, and to record the current of the test in real time. Naturally, the motor controller 142 and the potentiostat 144 may be integrated into a single device; typically a computer based multi-channel control system.

During the testing procedure a reference potential is established in the assembly 200 via the common reference electrode 124, a current is generated through the testing solution between the counter electrode 110 and the working electrode 106 within each testing cell 100 while the working electrode 106 is rotated at a desired speed by the associated rotator 140. Through sweeping the potential, current density of the electrochemical reaction on the working electrode surface can be measured, which offers valuable information about the kinetics of the reaction.

Due to the electrical connection with the testing solution, the single reference electrode 124 is common to each of the testing cells 100, greatly reducing the costs, set-up work, and time associated with each testing procedure. Moreover, the multiple tests simultaneously conducted will inherently have identical testing environments, which leads to more consistent results.

Figure 8:
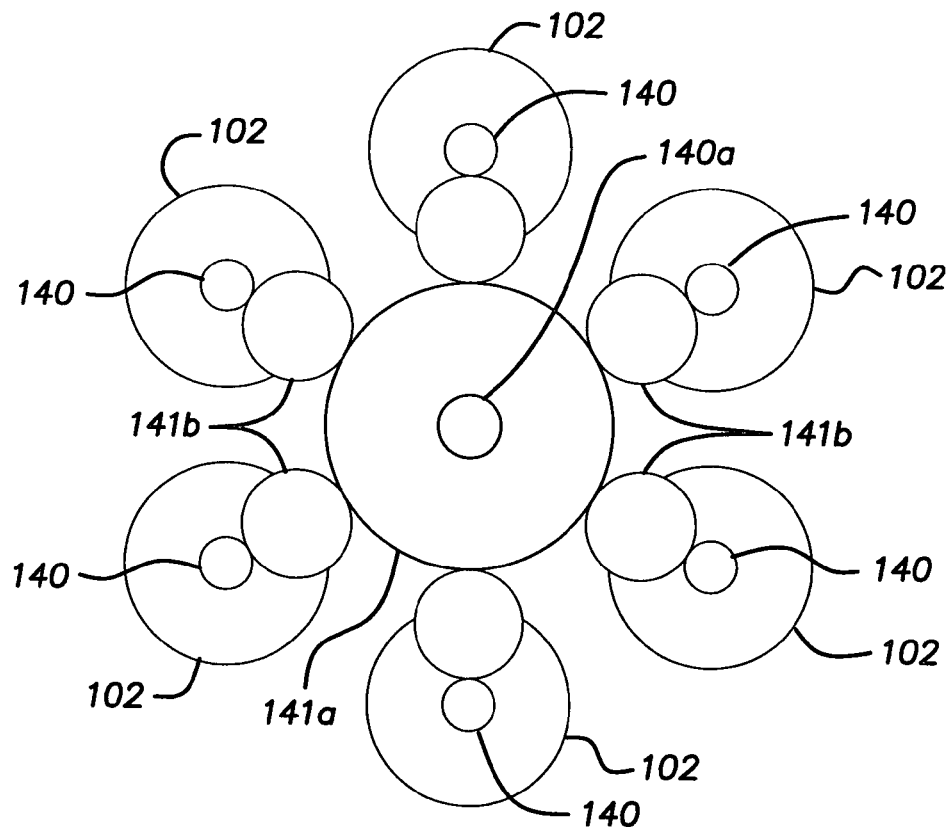
FIG. 8 schematically illustrates the assembly of FIG. 5 with a magnetic or mechanical coupling to drive the working electrodes.

While the present invention has been described with particularity herein, it is considered apparent that numerous modifications, rearrangements, and substitutions of parts may be resorted to without departing from the scope and spirit of the present invention. For example, instead of providing individual motors for each working electrode, it is contemplated that a single motor may be used to more reliably and accurately drive each working electrode. This alternative is schematically illustrated in FIG. 8, wherein a single motor 140a (i.e., master motor) is linked to the rotators 140 by a coupling 141a, 141b. The coupling 141a, 141b may be mechanical (i.e., gears, toothed drive belts, etc.) or may be magnetic. With this arrangement, only one motor 140a is required and the rotators 140 and associated working electrodes will be reliably and consistently driven at identical rotational speeds. Accordingly, control over the electrochemical cell assembly 200 is greatly simplified.

Accordingly, the present invention is not to be limited by the currently preferred embodiments described herein, but rather is only to be defined by the claims appended hereto.

What is claimed is:

1. An electrochemical cell assembly, comprising:
 a plurality of testing cells, each of said testing cells including a working electrode and a counter electrode, wherein said working electrode is selected from the group consisting of rotating disk electrodes and ring-disk electrodes;

a reference cell, said reference cell including a reference electrode;

a plurality of fluid connections for connecting each of said plurality of testing cells with said reference cell; and wherein said assembly further comprises a plurality of rotators, each of said rotators being associated with one of said working electrodes.

2. The electrochemical cell assembly according to claim 1, wherein said rotators are motors.

3. The electrochemical cell assembly according to claim 2, further comprising a controller, said controller being connected to said plurality of motors and being operable to control a speed of each of said motors so as to rotate said working electrodes at a desired rotational speed.

4. The electrochemical cell assembly according to claim 3, wherein the speed of rotation of each of said working electrodes is independently controlled.

5. The electrochemical cell assembly according to claim 1, wherein said plurality of testing cells, said reference cell, and said fluid connections each hold a testing solution.

6. The electrochemical cell assembly according to claim 5, wherein said fluid connections are provided by pipes extending between said reference cell and said testing cells.

7. The electrochemical cell assembly according to claim 6, wherein said pipes are siphon-type fluid connections.

8. The electrochemical cell assembly according to claim 1, wherein said reference electrode serves as a common reference electrode for each of the plurality of testing cells.

9. A method for testing plural chemical compositions in an electrochemical cell assembly according to claim 1, comprising the steps of:

filling said testing cells and said reference cell a predetermined amount with a testing solution;

rotating each of said working electrodes at a predetermined speed;

applying a reference potential to said testing solution via the reference electrode;

developing a current in said testing solution between each of the counter electrodes and an associated one of said working electrodes; and, measuring a current at each of the working electrodes;

using the measured current at defined potential to determine intrinsic kinetic properties of said chemical compositions.

10. The method according to claim 9, wherein the working electrodes are rotated at a common speed.

11. The method according to claim 9, comprising the further step of wherein the working electrodes are rotated at different speeds.

12. An electrochemical cell assembly, comprising:

a plurality of testing cells, each of said testing cells including a working electrode and a counter electrode wherein said working electrode is selected from the group consisting of rotating disk electrodes and ring-disk electrodes;

a reference cell, said reference cell including a reference electrode wherein said reference electrode serves as a common reference electrode for each of the plurality of testing cells;

a plurality of fluid connections for connecting each of said plurality of testing cells with said reference cell; and wherein said assembly further comprises a plurality of motors, each of said motors being associated with one of said working electrode.

13. The electrochemical cell assembly according to claim 12, further comprising a controller, said controller being connected to said plurality of motors and being operable to control a speed of each of said motors so as to rotate said working electrode at a desired rotational speed.

14. The electrochemical cell assembly according to claim 13, wherein the speed of rotation of each of said working electrodes is independently controlled.

15. The electrochemical cell assembly according to claim 13, wherein said plurality of testing cells, said reference cell, and said plurality of fluid connections each hold a testing solution.

16. The electrochemical cell assembly according to claim 15, wherein said fluid connections are provided by pipes extending between said reference cell and said testing cells.

17. The electrochemical cell assembly according to claim 15, wherein said pipes are siphon-type fluid connections.

18. An electrochemical cell assembly, comprising:

a plurality of testing cells, each of said testing cells including a working electrode and a counter electrode;

a reference cell, said reference cell including a reference electrode, said reference electrode serving as a common reference electrode for each of the plurality of testing cells;

a plurality of fluid connections for connecting each of said plurality of testing cells with said reference cell, a plurality of rotators, each of said rotators being associated with one of said working electrodes; and, a motor that is adapted to rotate each of said rotators.

19. The electrochemical cell assembly according to claim 18, wherein said motor is mechanically coupled to each of said rotators.

20. The electrochemical cell assembly according to claim 18, wherein said motor is magnetically coupled to each of said rotators.

* * * * *